(12) United States Patent
Mathieu et al.

(10) Patent No.: US 7,875,076 B2
(45) Date of Patent: *Jan. 25, 2011

(54) INTERVERTEBRAL IMPLANT

(75) Inventors: Claude Mathieu, Zurich (CH);
Christopher Marden John Cain, Eastwood (AU)

(73) Assignee: Synthes USA, LLC, West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/574,222

(22) Filed: Oct. 6, 2009

(65) Prior Publication Data

US 2010/0094421 A1  Apr. 15, 2010

Related U.S. Application Data

(63) Continuation of application No. 11/751,757, filed on May 22, 2007, now Pat. No. 7,618,456, which is a continuation of application No. 10/923,534, filed on Aug. 19, 2004, now Pat. No. 7,232,464, which is a continuation of application No. PCT/CH02/00099, filed on Feb. 19, 2002.

(51) Int. Cl.
*A61F 2/44* (2006.01)
(52) U.S. Cl. .................................. 623/17.11
(58) Field of Classification Search .... 623/17.11–17.16
See application file for complete search history.

(56) References Cited

U.S. PATENT DOCUMENTS

2002/0082597 A1 * 6/2002 Fraser ........................ 606/61

2005/0033433 A1 * 2/2005 Michelson ............... 623/17.11

OTHER PUBLICATIONS

Co-Pending U.S. Appl. No. 11/199,599—Preliminary Amendment dated Jan. 9, 2008.
Co-Pending U.S. Appl. No. 11/199,599—Non-Final Office Action dated Apr. 1, 2009.
Co-Pending U.S. Appl. No. 11/199,599—Interview Summary including Draft Claim Amendments dated Sep. 24, 2009.
Co-Pending U.S. Appl. No. 11/199,599—Amendment dated Sep. 29, 2009.
Co-Pending U.S. Appl. No. 11/199,599—Final Office Action dated Dec. 24, 2009.
Co-Pending U.S. Appl. No. 11/199,599—Appeal Brief dated Apr. 15, 2010.

* cited by examiner

*Primary Examiner*—Bruce E Snow
(74) *Attorney, Agent, or Firm*—Stroock & Stroock & Lavan LLP

(57) ABSTRACT

The intervertebral implant is in the form of a three-dimensional structure (10) comprising (a) a top side (1) and an underside (2) which are designed to rest against the end plates of two adjacent vertebras, (b) a left side face (3) and a right side face (4), (c) a front face (5) and a rear face (6), (d) a horizontal center plane situated between the top side (1) and the underside (2), (e) a vertical center plane (8) situated between the left side face (3) and the right side face (8) and (f) a plurality of boreholes (9) passing through the implant structure (10) that are designed to receive longitudinal affixation elements (20), the axes (19) of said elements intersecting the horizontal center plane (7). At least one of the boreholes (9) is designed in a manner that the affixation element (10) received in it can be rigidly connected to the intervertebral implant. Said connection is implemented using a thread or by matching conical surfaces.

16 Claims, 3 Drawing Sheets

INTERVERTEBRAL IMPLANT

CROSS-REFERENCE TO RELATED APPLICATIONS

This application is a continuation of U.S. patent application Ser. No. 11/751,757, now U.S. Pat. No. 7,618,456, filed May 22, 2007, which is a continuation of U.S. patent application Ser. No. 10/923,534, now U.S. Pat. No. 7,232,464, filed Aug. 19, 2004, which is a continuation of International Application No. PCT/CH02/00099, filed Feb. 19, 2002. The entire contents of these applications are expressly incorporated herein by reference thereto.

FIELD OF THE INVENTION

The present invention relates to an intervertebral implant.

BACKGROUND OF THE INVENTION

Such an intervertebral implant is known from the British patent document 2,207,607 A which discloses a horseshoe implant structure having a plurality of cylindrical holes. These holes are fitted with inner, smooth surfaces and comprise only one stop for the heads of the bone screws to be inserted into them. This design incurs the drawback that the inserted affixation screws may be anchored into the bone only by their shanks, a rigid connection with the horseshoe shaped intervertebral implant being lacking. As soon as the anchoring of the bone screw in the bone is weakened, the intervertebral implant becomes displaceable relative to the screw and the bone screws may then migrate while endangering the blood vessels. Moreover the loosening of the intervertebral implant may entail pseudoarthrosis.

The above cited state of the art is intended merely to elucidate the background of the present invention but it does imply that the cited state of the art had actually been made public or was publicly known at the time of this application or at the time of its priority.

BRIEF SUMMARY OF THE INVENTION

The objective of the present invention is palliation. This invention creates an intervertebral implant which is able to rigidly connect to bone affixation means in a manner that even in the event of bone structure weakening, loosening between the intervertebral implant and the bone affixation means shall be precluded.

The above problem is solved in the present invention by an intervertebral implant exhibiting the features of claim 1.

The advantages offered by the present invention substantially are attained by the rigid, that is by the firm connection between the intervertebral implant and the longitudinal affixing elements. Basically two different embodiment modes are available to attain said rigid connection.

In a first embodiment mode, at least one of the boreholes shall be internally threaded. In this case a matching bone screw fitted with a thread head may be rigidly screwed into the implant.

As regards a second embodiment mode, a front plate is mounted at the front surface of the three dimensional (3D) implant structure so as to be configured vertically to the horizontal center plane of the intervertebral implant, said boreholes passing through said front plate and receiving the anchored longitudinal affixation elements. Compared to the state of the art of a two-part implant, wherein a front plate is implanted in a separate operational step, the above design of the present invention offers the advantage that the intervertebral implant shall be implanted in a single step and hence in a simple and quicker manner. The invention offers a further advantage in that the intervertebral implant shall be affixed as frontally to the vertebra as possible, namely at a place where good bone material may be expected to be. As a result anterior displacement is restricted without thereby incurring greater danger to the surrounding structures than when using a state of the art intervertebral implant. The load still is being borne by the compressed vertebral implant, not by the front plate or the affixation screws.

In yet another embodiment mode of the present invention, the front plate is displaceably configured in the 3D implant structure in order that it may move vertically relative to this 3D implant structure. "Stress shielding" is attained in this manner (namely protection from or neutralization of mechanical stresses), and as a result the end plates may gradually match the intervertebral implant during the healing process.

As regards a further embodiment, the front plate is made of a material different from that of the 3D implant structure.

As regards a further embodiment of the present invention, at least one borehole tapers conically towards its underside and as a result a bone screw fitted with a matching conical head may be rigidly anchored in said borehole. Preferably the conical borehole exhibits a cone angle smaller than the resultant angle of friction. Appropriately the borehole's conicity shall be 1:3.75 to 1:20, preferably 1:5 to 1:15.

As regards a further embodiment mode of the present invention, the intervertebral implant side faces shall all be substantially convex.

Appropriately the intervertebral implant's top and/or undersides are not planar but convex. In this manner better matching to the end plates of the adjacent vertebras may be attained.

The boreholes preferably shall not pass through the left and right intervertebral implant side faces. Preferably again no borehole shall run through the front surface.

As regards a further preferred embodiment mode of the present invention, at least two boreholes shall be mutually parallel. This features facilitates inserting the vertebral implant during implantation.

As regards another preferred embodiment mode of the present invention, at least two boreholes shall run in mutually divergent manner as seen from the front side. As a result the bone screws shall move into a vertebral region offering better bone quality than found at the vertebra's center. Appropriately the borehole axes subtend an angle of 25 degrees to 70 degrees, preferably 35 degrees to 55 degrees with the horizontal center plane. This feature offers improved access for screw insertion.

As regards a further embodiment mode of the present invention, the boreholes shall not cross the horizontal center plane.

Depending on circumstance, two, three, four or even more longitudinal affixation elements may rigidly connected to the intervertebral implant; appropriately at least one affixation element shall pass through the top side and at least one affixation element shall pass through the intervertebral implant side.

Preferably the longitudinal affixation elements shall be bone screws comprising a head and a shank, said head preferably being fitted with an external thread that matches the inner thread of the intervertebral implant's borehole. As regards a second appropriate connection, preferably a bone screw shall be used of which the head tapers conically in the direction of the shank, the head's conicity corresponding to that of the intervertebral implant's borehole.

Regarding a further embodiment mode, at least two longitudinal affixation elements pass through the top side and at least two longitudinal affixation elements pass through the underside. In this manner the intervertebral implant is optimally anchored into the adjacent vertebras.

Preferably the screw-shaped longitudinal affixation elements exhibit a self-boring and self-tapping external thread. The longitudinal affixation elements also may be designed as unthreaded cylindrical pins fitted with a boring tip, preferably in the form of a trocar.

In another embodiment variation, the longitudinal affixation elements are spiral springs; lastly said longitudinal affixation elements also may be designed as single or multi-wing spiral blades.

In a further embodiment mode of the present invention, the longitudinal affixation element tip may be anchored in the structure of the intervertebral implant, as a result of which the head of the longitudinal affixation element may be anchored in the adjacent vertebra.

In a further embodiment mode of the present invention, the longitudinal affixation element head exhibits a widened diameter; also a support disk is provided for said head to rest against the vertebra.

The intervertebral implant may be made of any physiologically compatible material, though appropriately the implant structure shall consist of a physiologically compatible plastic, preferably an unreinforced plastic. The advantage offered by the invention over the already known, fiber-reinforced plastics used in implantology is that no reinforcing fibers will be bared—an eventuality that would be clinically disadvantageous. Appropriately bone screws consisting of non-reinforced plastic of which the external threads exhibit load bevels of 11 degrees to 14 degrees, preferably 12 degrees to 13 degrees, may be used in such an implant structure. The relatively small slope of the load bevel implements high clamping forces, as a result of which radial elongation and danger of cracking of the plastic are reduced. Appropriately the bone screws' external thread exhibits the bones at an angular pitch of 6 degrees to 10 degrees, preferably 7 degrees to 9 degrees. This particular angular pitch produces thread self-locking and prevents the bone screw from loosening on its own.

The borehole may be in the form of a metal bush fitted with an inner thread for the purpose of improving anchoring the bone screw in the plastic implant structure. The intervertebral implant also may consist partly of plastic and, in the borehole zones, of metal. This design offers improved guidance and anchoring of the bone screw in the intervertebral implant.

As regards a further preferred embodiment mode, the inside borehole walls are smooth, the thread head of a metallic, longitudinal affixation element cutting or tapping into said smooth wall.

BRIEF DESCRIPTION OF THE SEVERAL VIEWS OF THE DRAWINGS

The present invention and further embodiment modes of it are elucidated below in relation to the partly schematic representation of two illustrative embodiments.

DETAILED DESCRIPTION OF THE INVENTION

Figure 1:
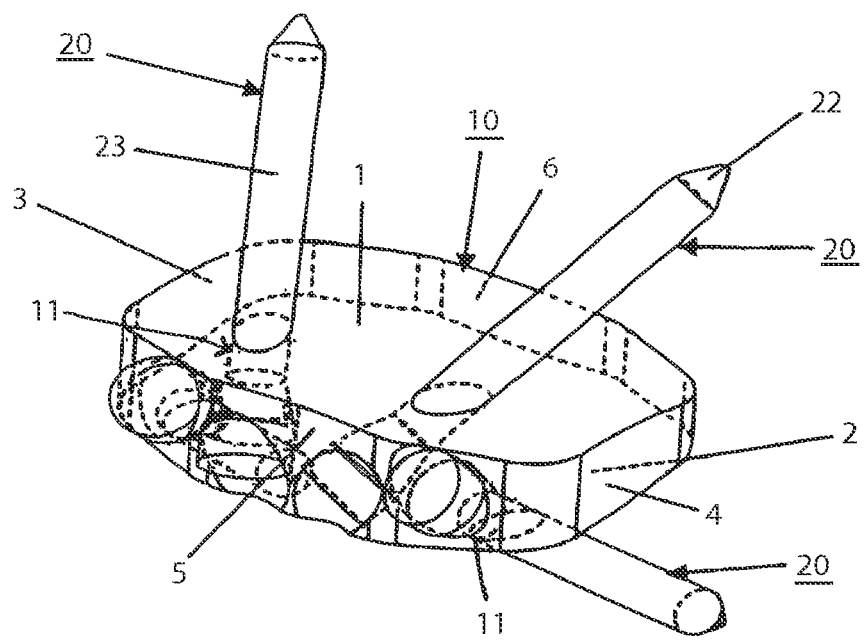
FIG. 1 is a perspective view including a partial section of the intervertebral implant with inserted bone screws.
Figure 2:
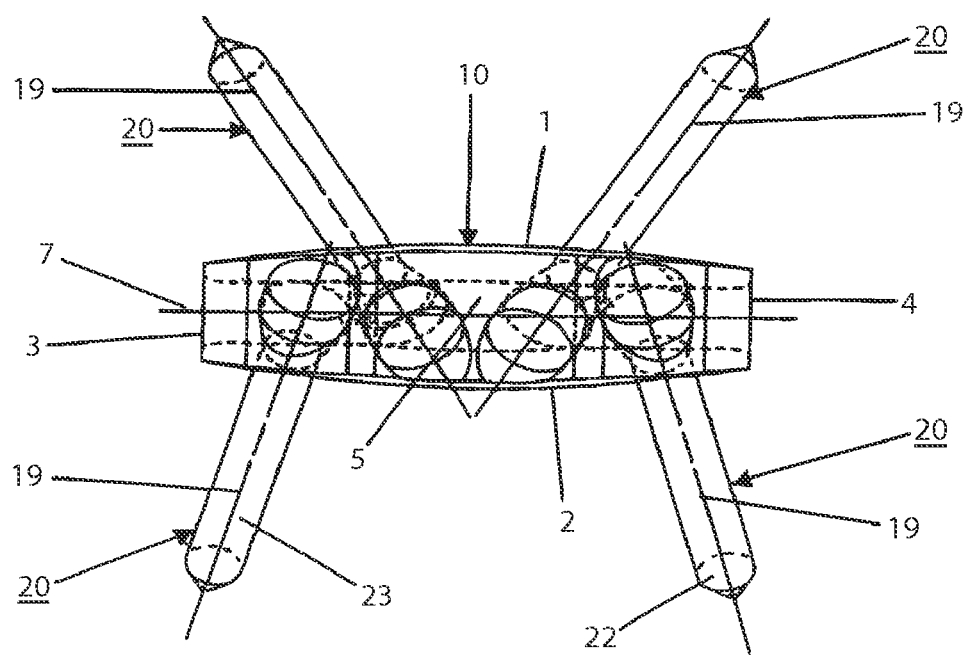
FIG. 2 is a front view of the intervertebral implant of FIG. 1.
Figure 3:
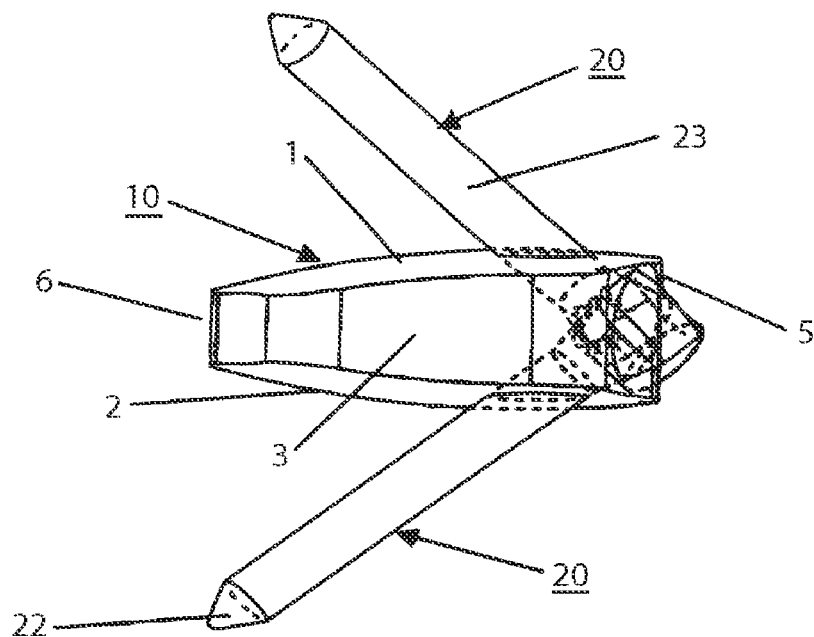
FIG. 3 is a side view of the intervertebral implant of FIG. 1.
Figure 4:
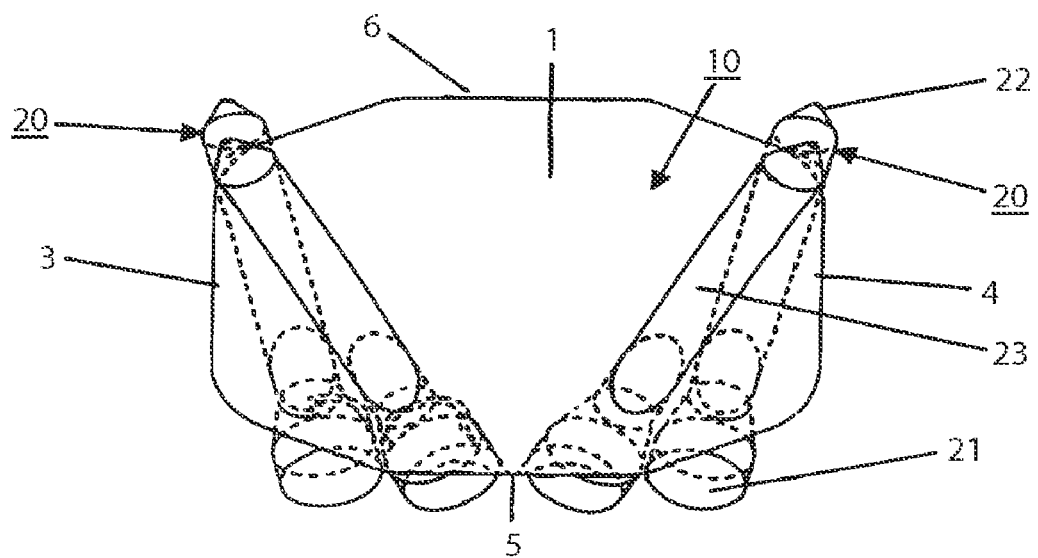
FIG. 4 is a top view of the intervertebral implant of FIG. 1.

The intervertebral implant of FIGS. 1 through 4 consists of a 3D structure 10 exhibiting both a convex top side 1 and a convex underside 2, the two sides each being designed to rest against the end plates of two adjacent vertebras. To attain improved anchoring, the top side 1 and the underside 2 may be topographically shaped and be fitted with grooves, ribs or teeth, or their surfaces may be merely roughened.

The 3D implant structure 10 moreover comprises a left side face 3 and a right side face 4, also a front face 5 and a rear face 6. The implant structure 10 also may be hollow and its outer surface may comprise perforations.

The implant structure 10 comprises a plurality of boreholes 9 passing through it and receiving longitudinal affixation elements 20. Preferably four such boreholes 9 shall be provided.

At least one of the boreholes 9 is designed in a way that the longitudinal affixation element 20 received therein may be rigidly connected to the intervertebral implant. The boreholes 9 are conical for that purpose.

Preferably the affixation elements 20 are bone screws having a head 21 and a tip 22. The head 21 conically tapers toward the shank 23, the conicity of the head 21 corresponding to the conicity of the borehole 9. Moreover the four boreholes 9 may be fitted with inner threads 11.

Figure 5:
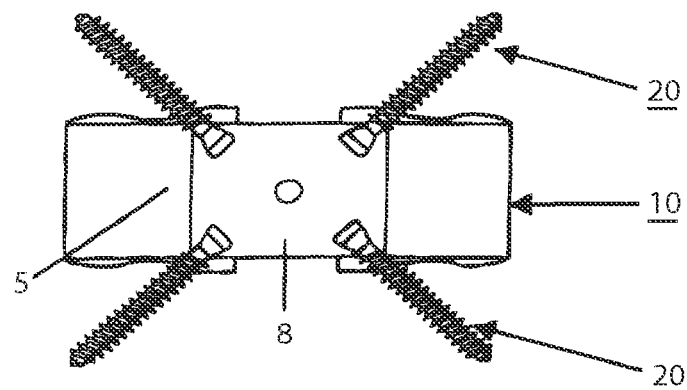
FIG. 5 is a front view of the intervertebral implant with a front insert, in partial section.
Figure 6:
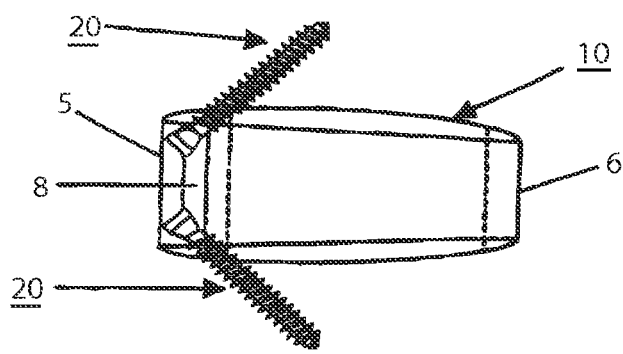
FIG. 6 is a vertical, longitudinal section of the intervertebral implant of FIG. 5.
Figure 7:
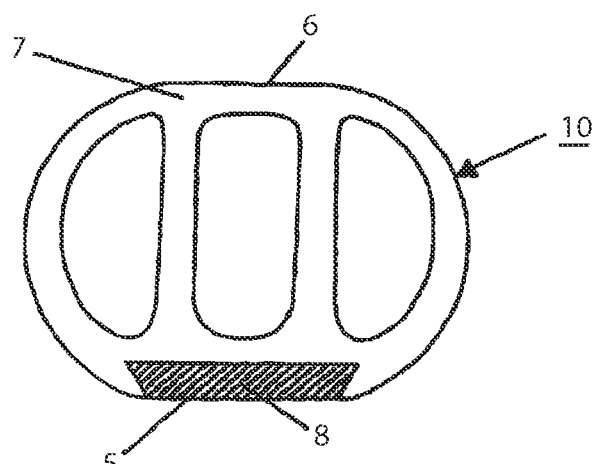
FIG. 7 is a horizontal cross-section of the intervertebral implant of FIG. 5.

As regards the embodiment variation shown in FIGS. 5 through 7, the 3D structure 10 is fitted at its front face 5 with a preferably metallic insert 8 into which the affixation elements 20 may be anchored. The insert 8 is mounted in vertically displaceable manner in the 3D structure 10.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

We claim:

1. An intervertebral implant for insertion between an upper vertebra having an upper endplate and a lower vertebra having a lower endplate, the implant comprising:

a body having a first lateral side surface, a second lateral side surface, a posterior face, an anterior face, an upper surface and a lower surface, the upper and lower surfaces being sized and configured to contact the upper and lower endplates, respectively, of the upper and lower vertebrae, the upper surface defining an upper plane and the lower surface defining a lower plane;

a plate operatively coupled to the body, the plate having a plate top surface located generally on the upper plane and a plate lower surface located generally on the lower plane when the plate is coupled to the body so that the body has a first height extending between the upper surface and the lower surface and the plate has a second height extending between the plate top surface and the plate lower surface, the second height being generally equal to the first height, first and second boreholes passing through the plate, the first and second boreholes positioned between the upper and lower planes; and first and second bone screws each having a head and a shank, the first bone screw being sized and configured to extend through the first borehole and into the upper endplate, the second bone screw being sized and configured to extend through the second borehole and into the lower endplate to anchor the intervertebral implant to the upper and lower vertebrae and the heads of the first and second bone screws positioned between the upper and lower planes.

2. The implant of claim 1, wherein the implant includes a plurality of teeth.

3. The implant of claim 1, wherein the plate contacts the anterior face of the body.

4. The implant of claim 3, wherein the anterior face of the body includes a recess for receiving the plate.

5. The implant of claim 1, wherein the plate is entirely contained between the endplates of the upper and lower vertebrae when the implant is inserted between the upper and lower vertebrae.

6. The implant of claim 1, wherein the body and the plate are pre-assembled so that the body and the plate are inserted between the upper and lower vertebrae as a single unit.

7. The implant of claim 1, wherein the implant includes a vertical center plane, the first and second fasteners being laterally divergent from the vertical center plane.

8. The implant of claim 1, wherein the body comprises a horizontal center plane and the plate is disposed substantially perpendicular to the horizontal center plane.

9. The implant of claim 1, wherein the body comprises a horizontal center plane and the plate is displaceable in a direction substantially perpendicular to the horizontal center plane.

10. The implant of claim 1, wherein the body is formed from a first biocompatible material and the plate is formed from a second biocompatible material, the second biocompatible material being different than the first biocompatible material.

11. The implant of claim 10, wherein the plate is made from a biocompatible metal and the body is made from a biocompatible plastic.

12. The implant of claim 1, wherein the body comprises a horizontal center plane and the first and second fastener holes have an axis angled from about twenty-five degrees (25°) to about seventy degrees (70°) with respect to the horizontal center plane.

13. The implant of claim 12, wherein the axis is angled from about thirty-five degrees (35°) to about fifty-five degrees (55°) with respect to the horizontal center plane.

14. The implant of claim 1, wherein the plate is slidably displaceable with respect to the body.

15. The implant of claim 1, wherein the first and second fasteners are bone screws and wherein the first and second fastener holes formed in the plate are internally threaded and the heads of the bone screws are externally threaded for engaging the internally threaded holes.

16. The implant of claim 1, wherein the plate further comprises a horizontal center midplane, the head of the first fastener being located between the top surface of the plate and the horizontal center midplane and the head of the second fastener being located between the bottom surface of the plate and the horizontal center midplane.

* * * * *